United States Patent [19]

Wandell

[11] Patent Number: Plant 7,036

[45] Date of Patent: Sep. 19, 1989

[54] GREEN ASH NAMED 'WASKY'

[76] Inventor: Willet N. Wandell, Rte. #1, Box 286, Oquawka, Ill. 61469

[21] Appl. No.: 165,576

[22] Filed: Mar. 7, 1988

[51] Int. Cl.[4] ..... A01H 5/00

[52] U.S. Cl. ..... Plt./51

[58] Field of Search ..... Plt./51

*Primary Examiner*—James R. Feyrer

[57] ABSTRACT

A male green ash tree having a strong central leader, strongly ascending uniformly spaced scaffold branches, uniform crotch angles, and heavy stems, forming an attractive, narrowly oval tree of compact appearance and low pruning requirements; further, the subject tree develops a heavy furrowed protective bark at an early age on the bole and branches progressing from smooth juvenile ash-gray bark slightly tinged with red. Fall foliage color is ephemeral turning to bronze-red with heavy autumn frosts.

6 Drawing Sheets

This new variety of green ash has its origin from seeds collected from a parent tree in 1965 at Danville, Ill., and grown in central Illinois. These seeds were planted and grew seedlings in Wandell Nursery in central Illinois. This variety was selected from the superior trees of this group and was outplanted by propagating by chip budding. I currently gave 300 trees growing in my nursery at Oquawka, Ill. propagated by chip budding, all maintaining the distinguishing characteristics of the original selection.

SUMMARY OF INVENTION

A new and distinct cultivar of green ash characterized by its narrow, upright, symmetrical dense crown; thick somewhat lustrous leaves; deep bronze-red fall color and thick protective bark that becomes deeply furrowed and ridged at an early age.

DESCRIPTION OF THE NEW PLANT

Figure 1:
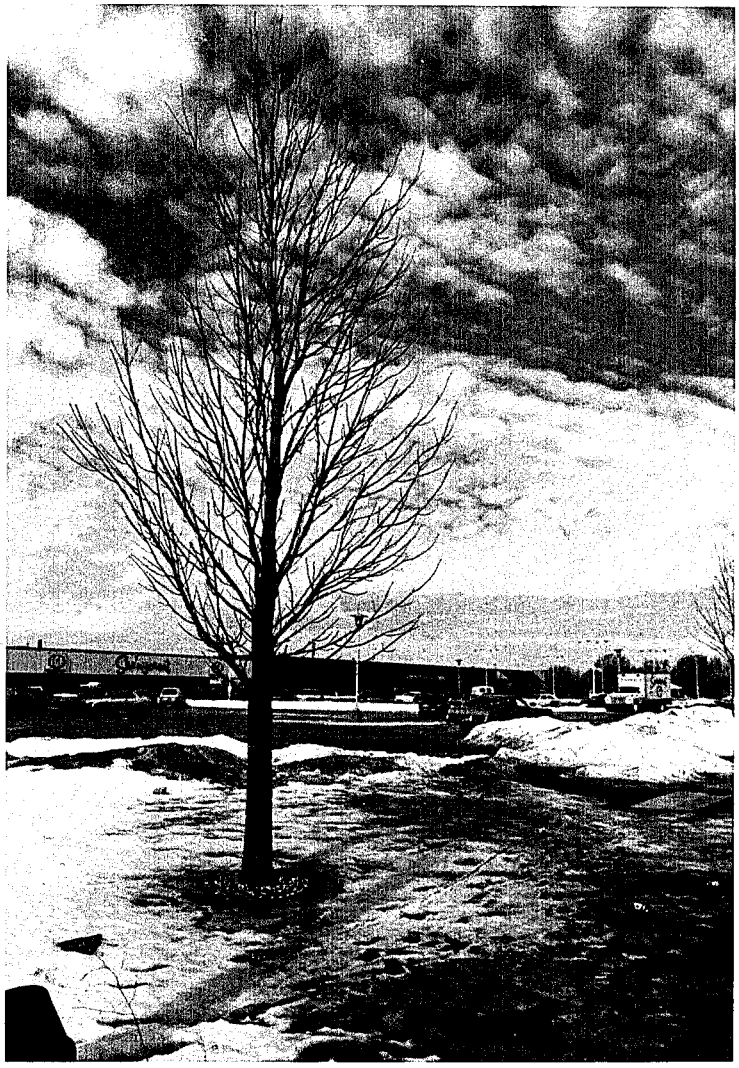
FIG. 1 is a photographic view of the dormant tree showing the strongly ascending branches 45 degrees from the bole of the tree and narrow, upright, symmetrical growth habit of the crown.
Figure 2:
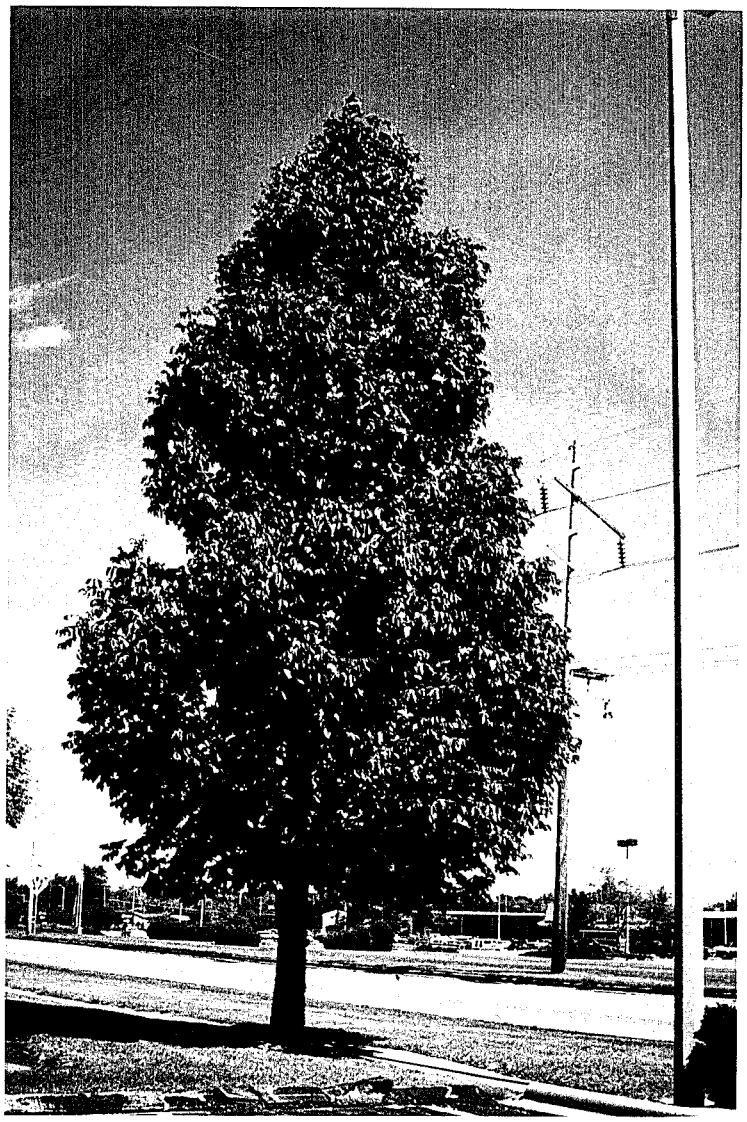
FIG. 2 is a photographic view of the tree in leaf and showing the dense leaf population, tight, neat appearance of the crown and thick lustrous qualities of the leaves.
Figure 3:
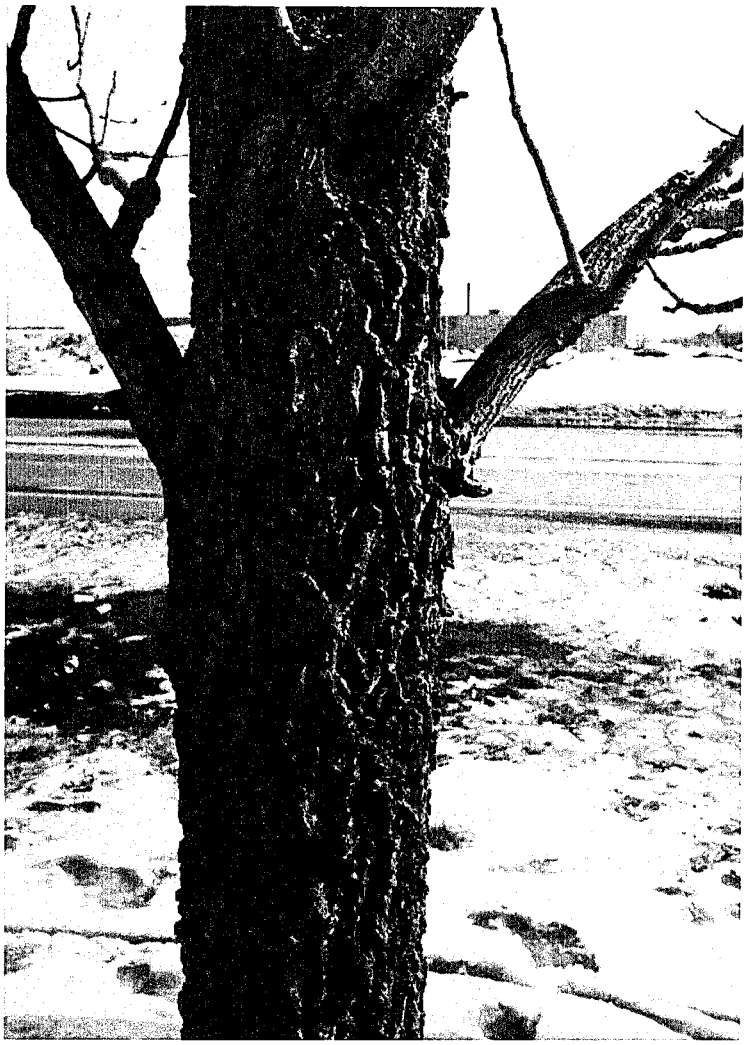
FIG. 3 is a photographic view of the bark of the tree that develops at an early age and characterized by pronounced scaly, flat-topped ridges separated by deep fissures.
Figure 4:
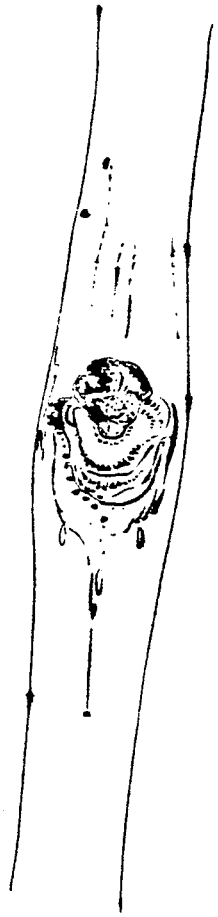
FIG. 4 is a drawing of the dormant bud showing the leaf scar.
Figure 5:
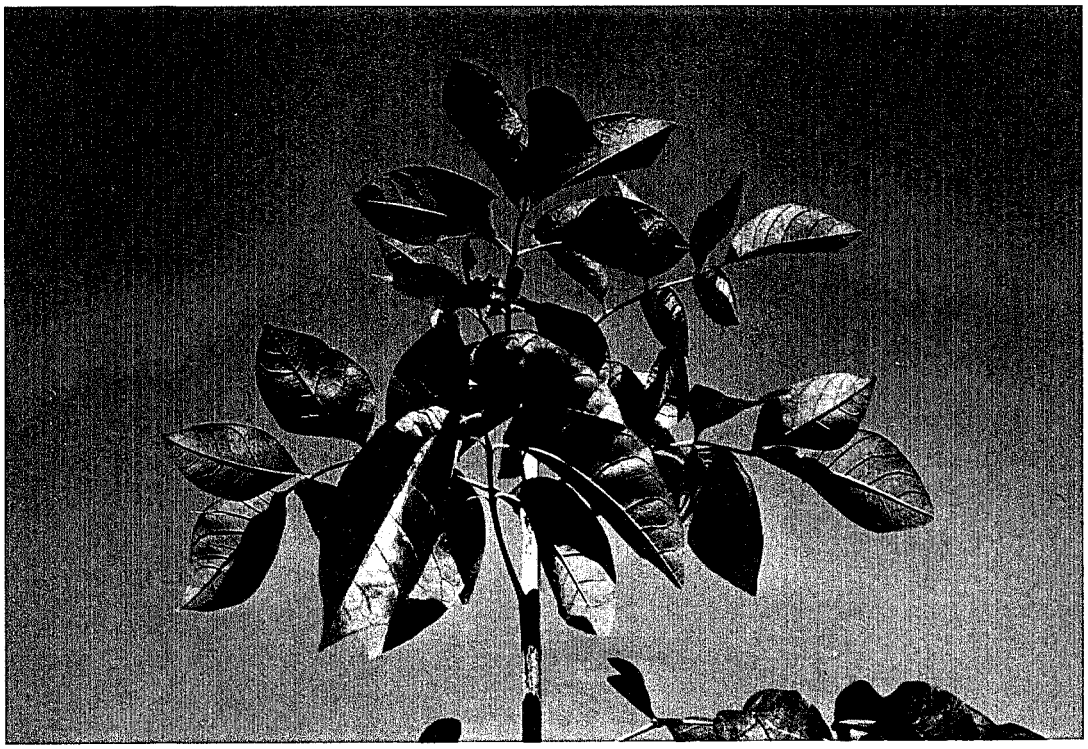
FIG. 5 is a photographic view of the leaves of subject plant showing a close-up of fall color.
Figure 6:
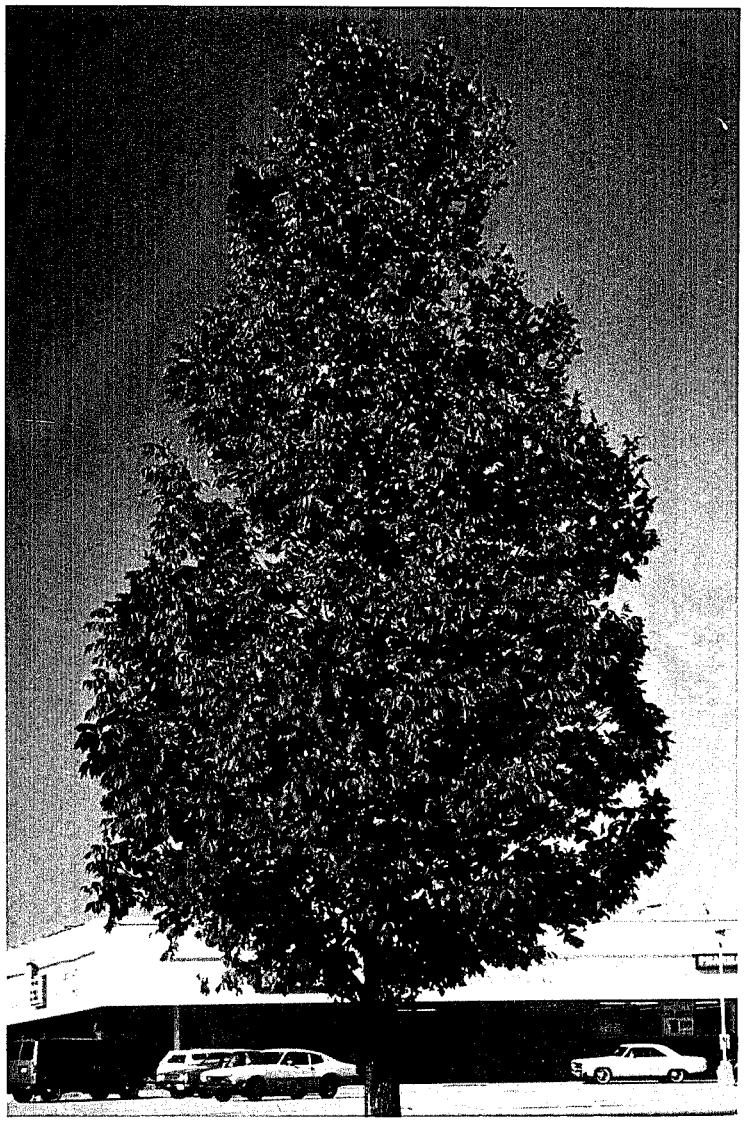
FIG. 6 is a photographic view of the entire subject plant showing fall color.

The following is a detailed description of my new cultivar with color designations according to the R.H.S. Colour Chart published by The Royal Horticultural Society of London, England and the stated observations having been made at Urbana, Ill. by applicant.

Origin: Seedling growing under cultivated conditions.

Parentage: A tree propagated from seeds collected at Danville, Ill. from a parent tree.

Propagation: Maintains its distinguishing characteristics when propagated by asexual propagation.

Classification: *Fraxinus pennsylvanica* 'Wasky'.

Form: Medium sized tree.

Habit: Deciduous tree with a single trunk and a straight, single leader; crown upright, narrowly oval in shape, symmetrical, densely filled with leaves; branches strongly ascending.

Growth rate: Moderately fast growing.

Bark: Thick and protective, dark gray, becoming deeply longitudinally furrowed at an early age, the ridges very pronounced, scaly, flat-topped, forming elongate, irregularly diamond-shaped patterns.

Leaves: Opposite, pinnately compound with 7 or 9, rarely 5, leaflets; rachis glabrous, faintly winged; leaflets ovate, slightly curving, 8–16 cm long and 4–6 cm broad, dark green (R.H.S. 139A) and semi-lustrous above, paler (R.H.S. 146B) below, turning bronze-red for a brief period in autumn (R.H.S. color charts red group 53A), somewhat coriaceous, glabrous except for a few hairs on the veins of the lower surface, the apices shortly acuminate, the margins essentially entire or with a few obscure teeth, the bases asymmetrical, rounded; petiolules short, 3–5 mm long, winged at least on one side.

Winter buds: Reddish-brown, 3–5 mm long, half-globose, with 2 or 3 pairs of opposite, overlapping bud scales, densely covered with tiny adpressed peltate scales; terminal bud present, broadly ovoid; stipule scars lacking.

Twigs: Stout, 5–7 mm in diameter, round, slightly swollen at the nodes, glaucous, marked with raised, round lenticels, first year stems medium brown and puberulent, older twigs gray and glabrous; leaf scars opposite, semicircular, nearly straight across the top, very conspicuous, 5–7 mm broad, with numerous bundle traces arranged in a C-shaped pattern.

Fruit: Plant is a male.

Flowers: Male flowers produced on the plant in limited quantities: apelitate, clasping, cup-shaped calyx with two stamens.

I claim:

1. A new and distinctive variety of *Fraxinus pennsylvanica* named 'Wasky' as described herein and as illustrated, that differs from all other varieties by the unique combination of: (1) strongly ascending branches and a narrow, upright, symmetrical crown that is densely filled with leaves, maintaining a neat appearance; (2) leaves that are dark green, thick and semilustrous above in summer, turning bronze-red for a brief period in autumn; and (3) thick, protective bark that at an early age develops pronounced scaly, flat-topped ridges separated by deep fissures. Flowers show male character and tree produces no seed.

* * * * *